Figure 1:
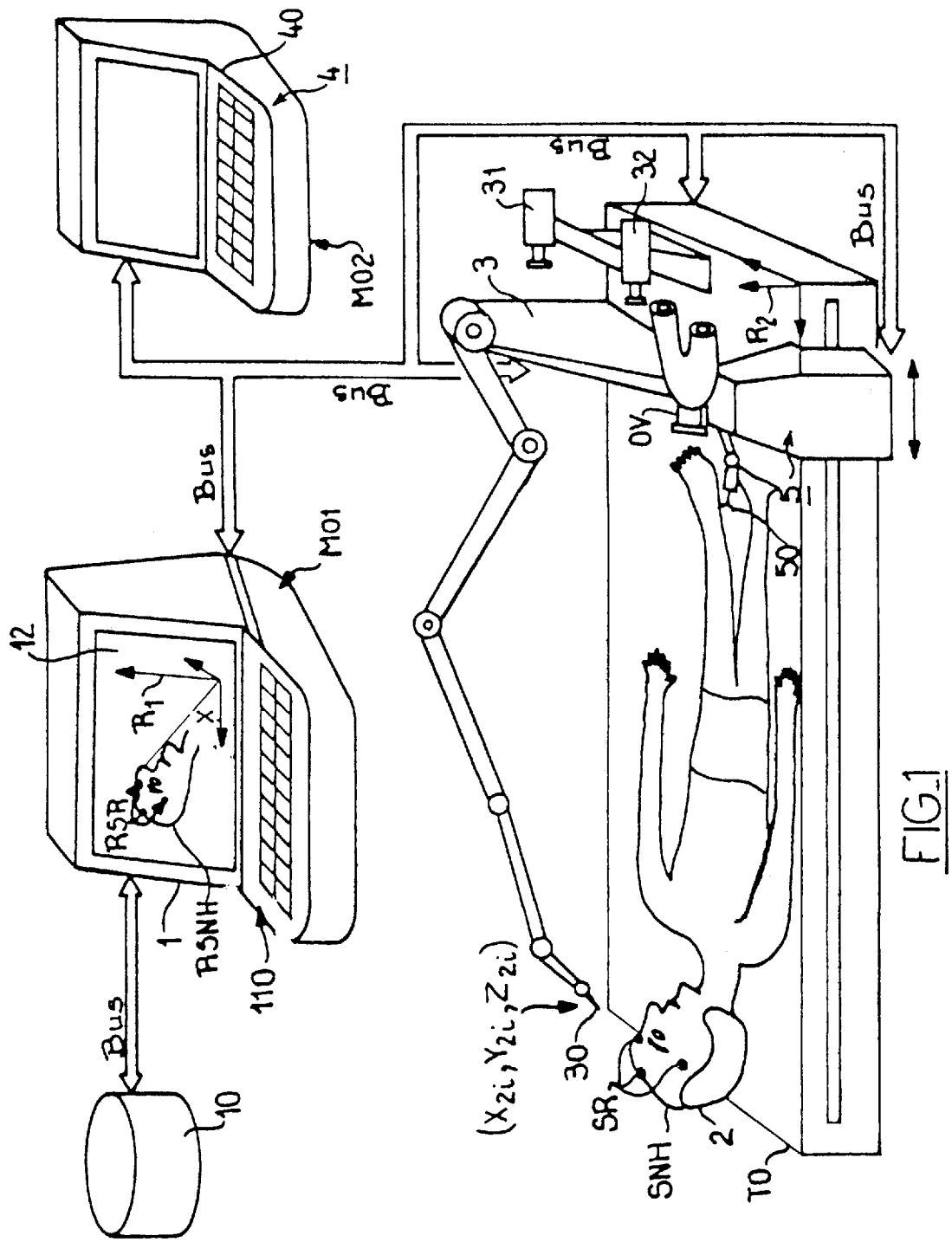

United States Patent [19]
Henrion et al.

[11] Patent Number: 5,868,675
[45] Date of Patent: *Feb. 9, 1999

[54] INTERACTIVE SYSTEM FOR LOCAL INTERVENTION INSIDE A NONHUMOGENEOUS STRUCTURE

[75] Inventors: Joël Henrion, Suippes; Michel Scriban, Ternay; Jean-Baptiste Thiebaut; Jean-François Uhl, both of Paris, all of France

[73] Assignee: Elekta IGS S.A., Gieres, France

[ * ] Notice: The terminal 36 months of this patent has been disclaimed.

[21] Appl. No.: 847,059

[22] PCT Filed: May 10, 1990

[86] PCT No.: PCT/FR90/00714

§ 371 Date: Jun. 22, 1992

§ 102(e) Date: Jun. 22, 1992

[87] PCT Pub. No.: WO91/04710

PCT Pub. Date: Apr. 18, 1991

[30] Foreign Application Priority Data

Oct. 5, 1989 [FR] France .................................. 89 13028

[51] Int. Cl.⁶ ...................................................... A61B 5/05
[52] U.S. Cl. ........................................... 600/424; 606/130
[58] Field of Search ............................. 128/653.1; 378/4, 378/20, 41, 58, 205; 606/130; 901/6, 16, 41; 600/407, 411, 415, 417, 424

[56] References Cited

U.S. PATENT DOCUMENTS

| | | | |
|---|---|---|---|
| 4,638,798 | 1/1987 | Shelden et al. | 606/130 |
| 4,791,934 | 12/1988 | Brunnett | 128/653.1 |
| 5,050,608 | 9/1991 | Watanabe et al. | 128/653.1 |
| 5,078,140 | 1/1992 | Kwoh | 128/653.1 |
| 5,143,076 | 9/1992 | Hardy et al. | 606/130 |
| 5,186,174 | 2/1993 | Schlöndorff et al. | 128/653.1 |
| 5,273,039 | 12/1993 | Fujiwara et al. | 600/407 |
| 5,280,427 | 1/1994 | Magnusson et al. | 606/130 |
| 5,285,787 | 2/1994 | Machida | 606/130 |
| 5,409,497 | 4/1995 | Siczek et al. | 606/130 |
| 5,572,999 | 11/1996 | Fubda et al. | 600/407 |

FOREIGN PATENT DOCUMENTS 0009151 12/1988 WIPO .
WO 88/09151 12/1988 WIPO .

OTHER PUBLICATIONS

Lavallee, S. A New System for Computer Assisted Neurosurgery. IEEE Engineering in Medicine & Biology Society 11th Annual International Conference, vol. 11, pp. 926–927, Nov. 1989.

Watanabe, E et al. Three–Dimenstional Digitizer (Neuronavigator): New Equipment for Computed Tomography–Guided Stereotaxic Surgery. Surg. Neurol., vol. 27, pp. 543–547, 1987.

(List continued on next page.)

Primary Examiner—Brian Casler
Attorney, Agent, or Firm—Blakely Sokoloff Taylor & Zafman

[57] ABSTRACT

An interactive system for a local intervention inside a region of a non-homogeneous structure, such as the skull of a patient, which is related to the frame of reference ($R_2$) of an operation table, and which is connected to a reference structure comprising a plurality of base points. The system creates on a screen a representation of the non-homogeneous structure and of the reference structure connected thereto, provides the coordinates of the images of the base points in the first frame of reference ($R_1$), allows the marking of the coordinates of the base points in $R_2$, and allows the carrying out of the local intervention with an active member such as a trephining tool, a needle, or a radioactive or chemical implant. The systems also optimizes the transfer of reference frames between $R_1$ and $R_2$, from the coordinates of the base points in $R_2$ and the images in $R_1$ by reducing down to a minimum the deviations between the coordinates of images in $R_1$ and the base points in $R_1$ after transfer. The system also establishes real time bi-directional coupling between: (1) an origin and a direction of intervention simulated on the screen, (2) the position of the active member.

16 Claims, 13 Drawing Sheets

OTHER PUBLICATIONS

Batnitzky, S. et al. Three–Dimensional Computer Reconstruction from Surface Contours for Head CT Examinations. J. Comp. Asst. Tomogr., vol. 5, No. 1, pp. 60–67, Feb. 1981.

Roberts, D.W., et al. A Frameless Stereotaxic Integration of Computerized Tomographic Imaging and the Operating Microscope. J. Neurosurg., vol. 65, pp. 545–549, 1986.

Kelly, P.J. et al. Computer–assisted Stereotactic Laser Microsurgery for the Treatment of Intracranial Neoplasms, Neurosurgery. vol. 10, No. 3, pp. 324–330, 1982.

S. Lavallee, "A New System for Computer Neurosurgery", IEEE Eng. in Medicine & Bio. Soc. 11th Annual Int. Conf., Nov. 9–12, 1989, pp. 926–927.

Watanabe et al., Three Dimensional Digitizer (Neuronavigator): New Equipment for Computed Tomography–Guided Stereotoxic Surgery, Surg. Neurol., 1987, No. 27, pp. 543–547.

P.J. Kelly et al., "Computer–Assisted Stereotactic Laser Micro–Surgery for the Treatment of Intracranial Neoplasms", Neuro., vol. 10, No. 3, 1982, pp. 324–330.

Batnitzky et al., "Three–dimensional Computer Reconstruction From Surface Contours for Head CT Examinations", Journal of Comp. Assisted Tomography, No. 5, Feb. 1981, pp. 60–67

Roberts et al., "A Frameless Stereotoxic Integration of Computerized Tomographic Imaging and the Operating Microsc gsl", J. of Neuro. Surg. No. 65, 1986, pp. 545–549.

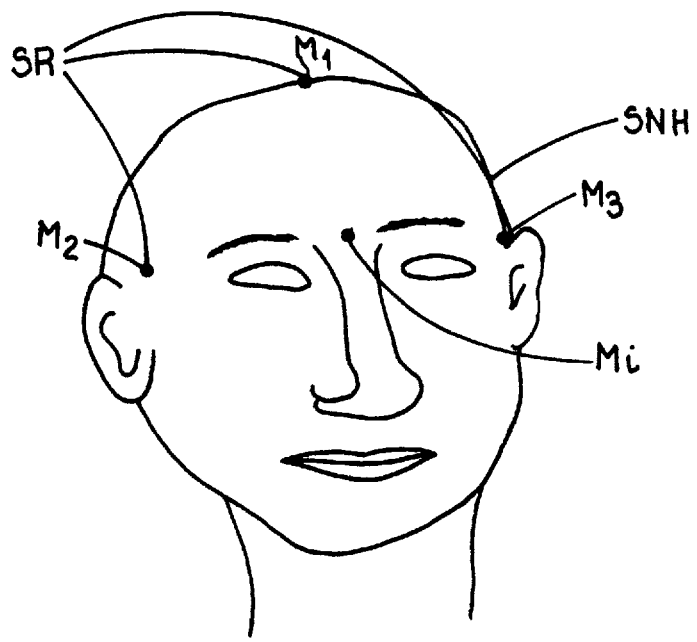
FIG_2
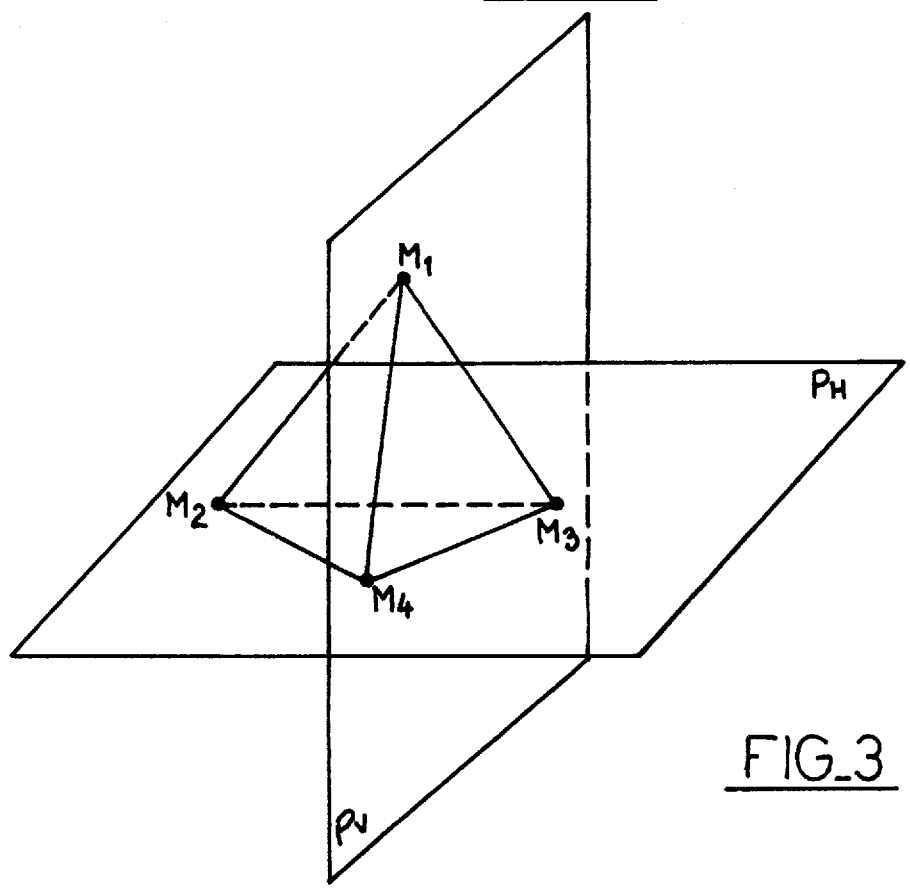
FIG_3

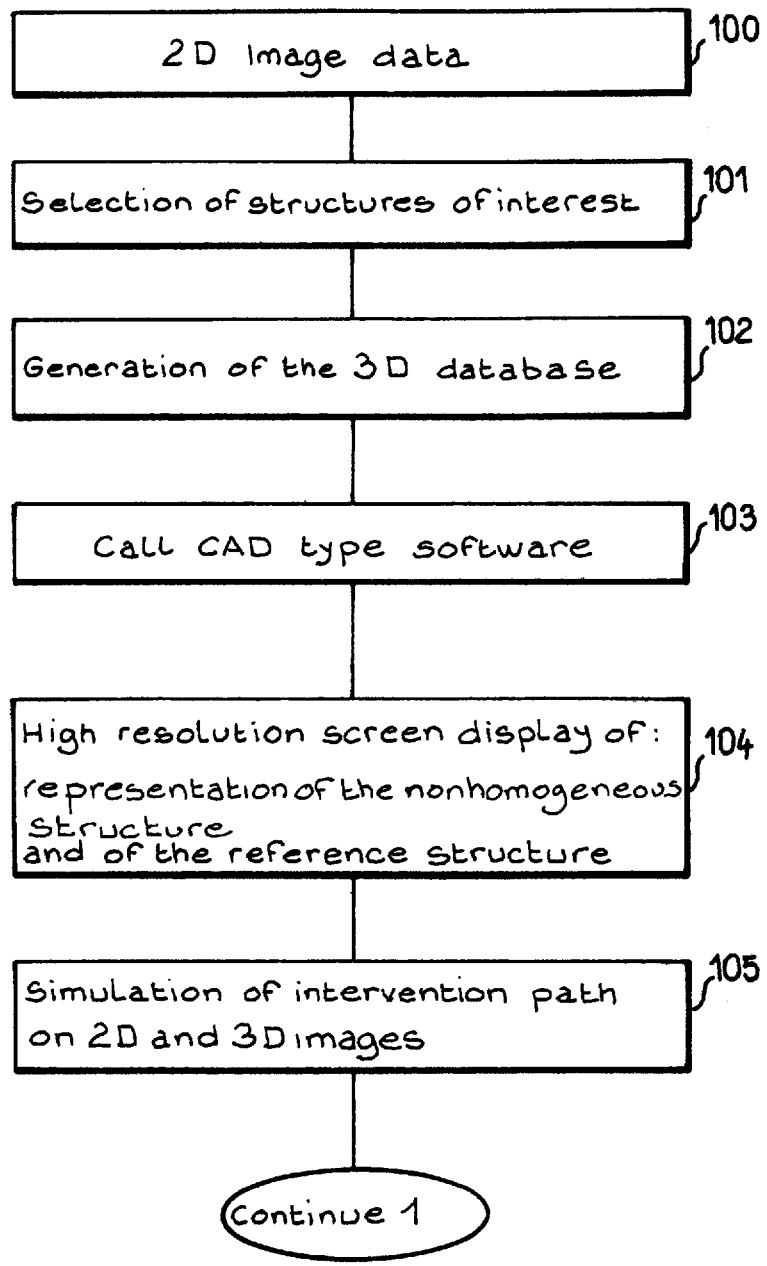
FIG_5a

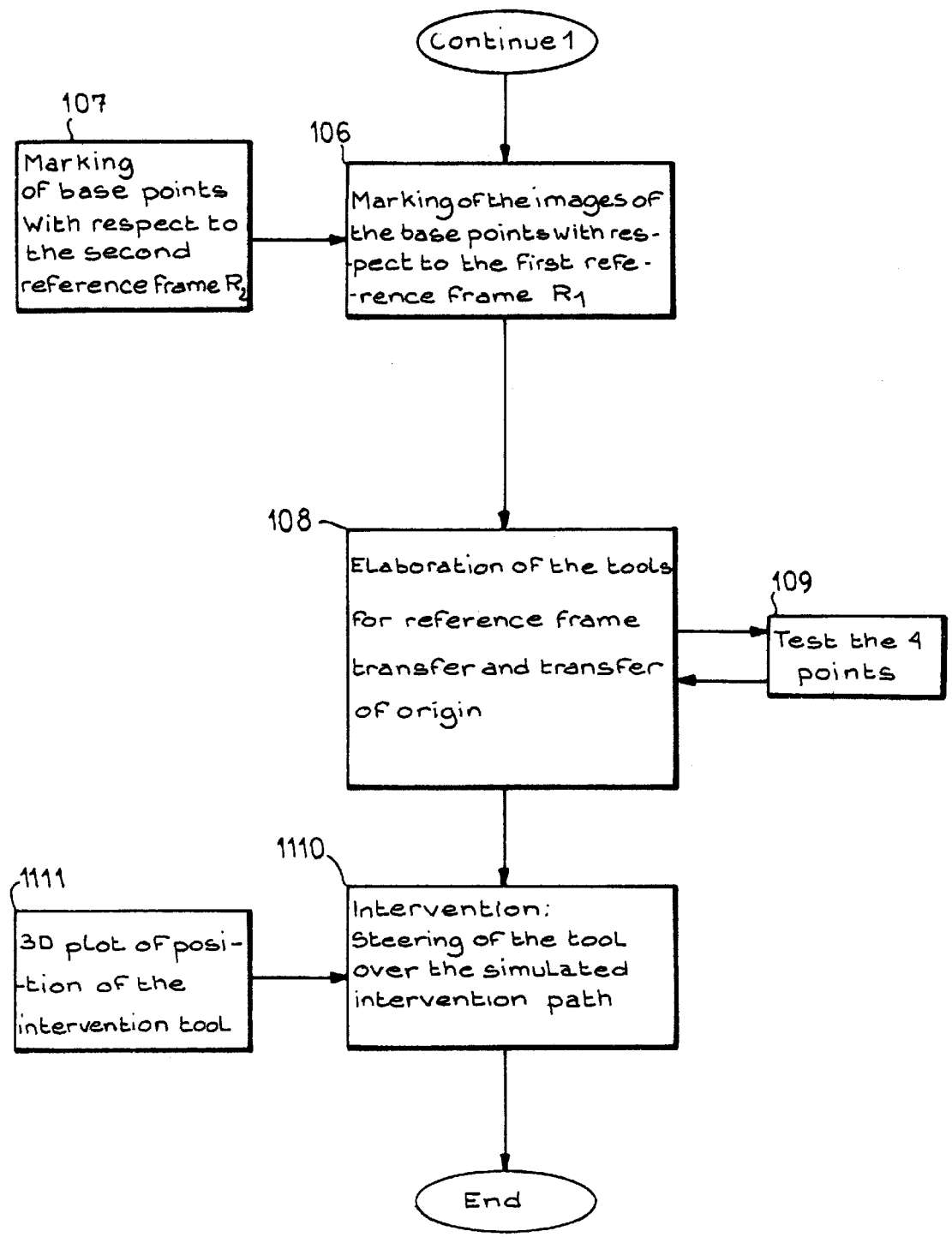
FIG_5b

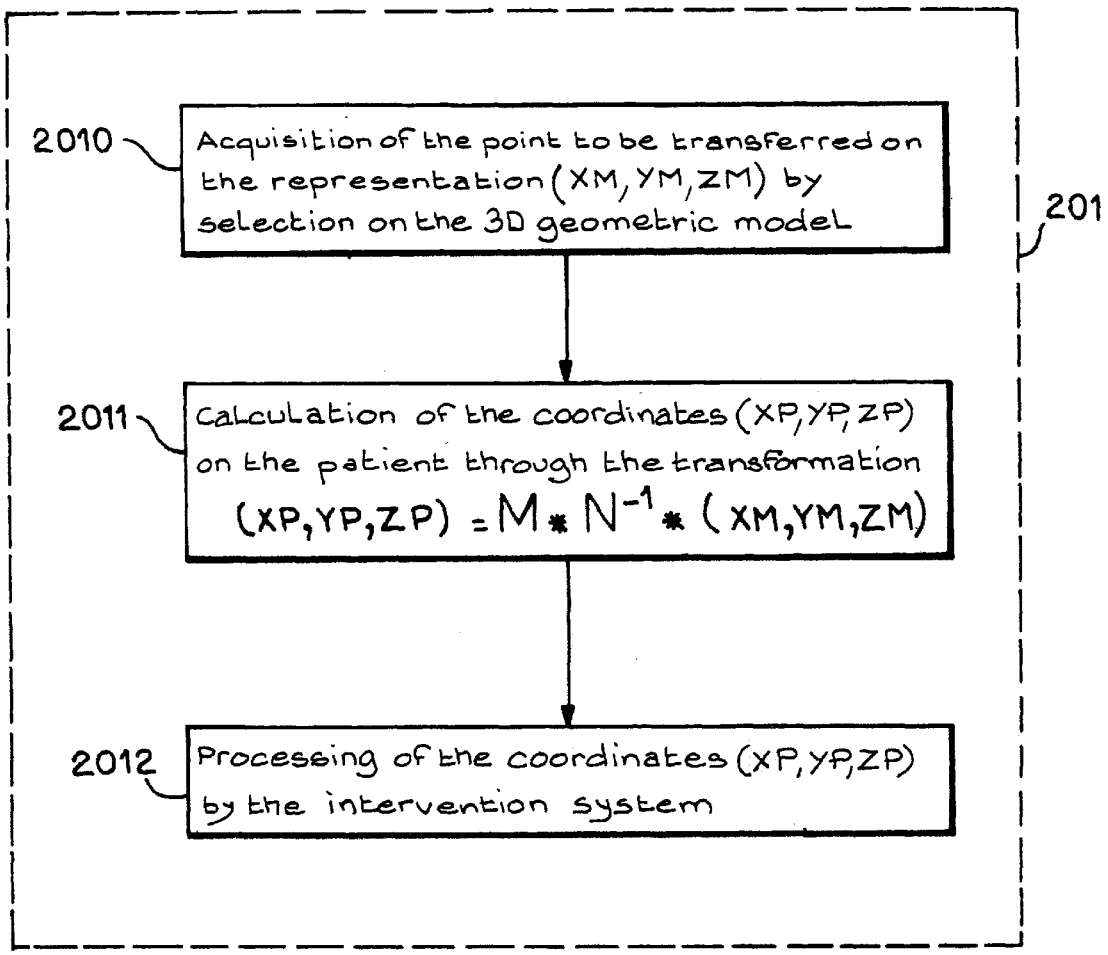
FIG_7

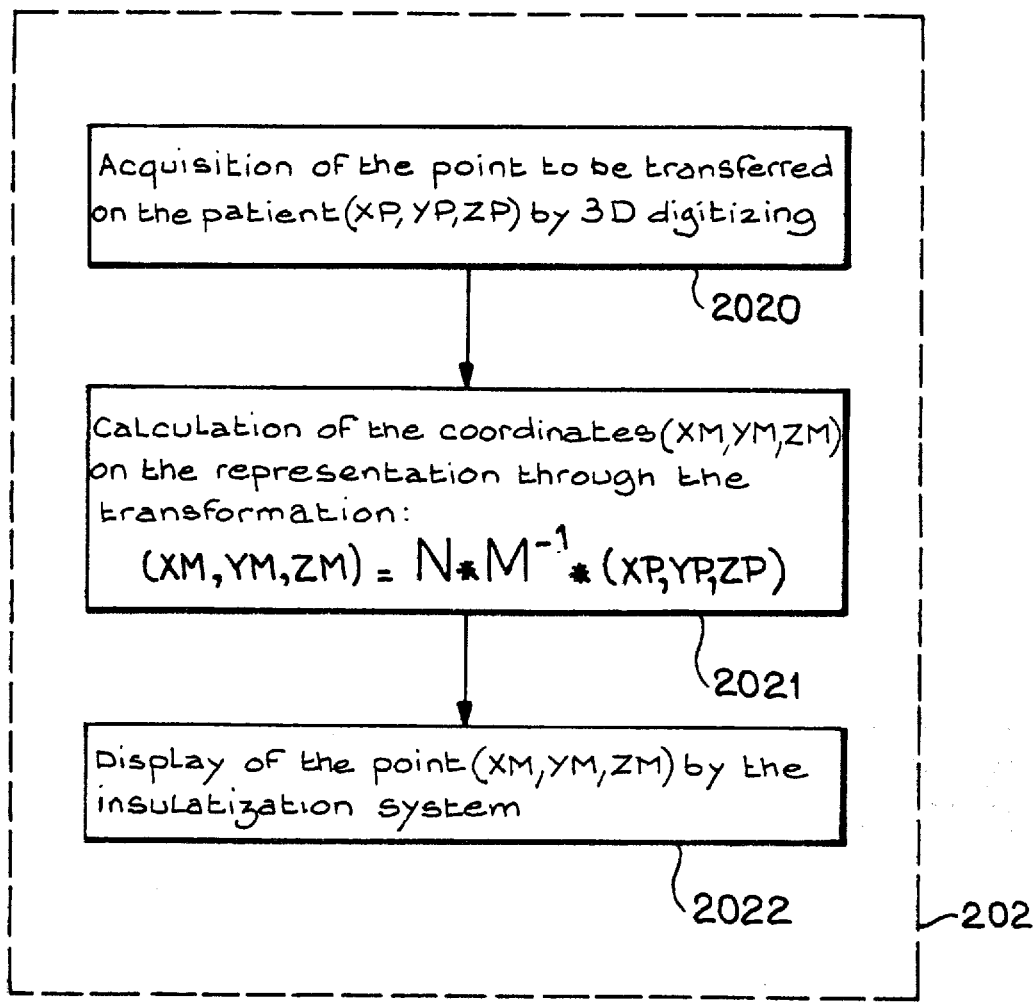
FIG_8

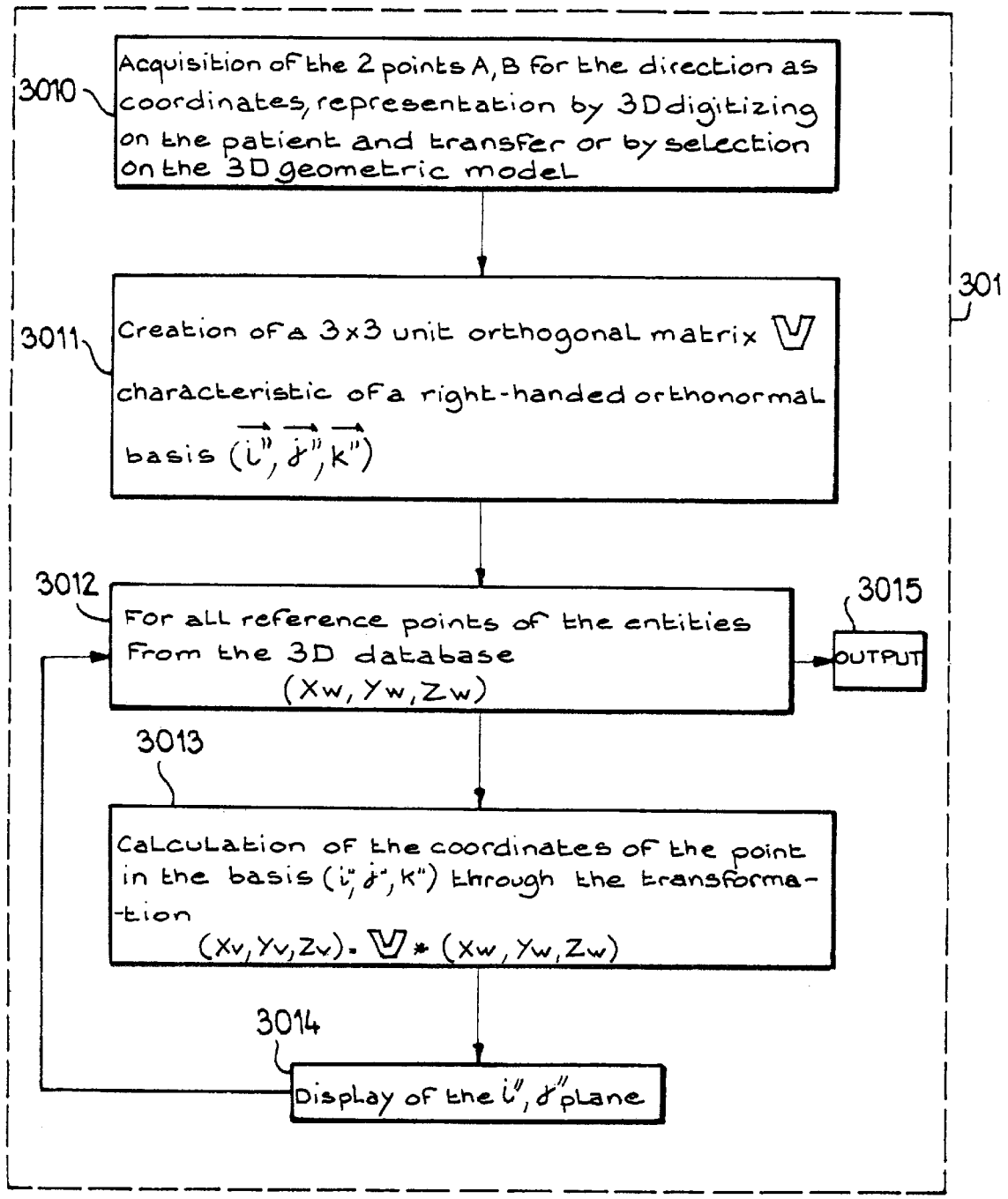
FIG_9a

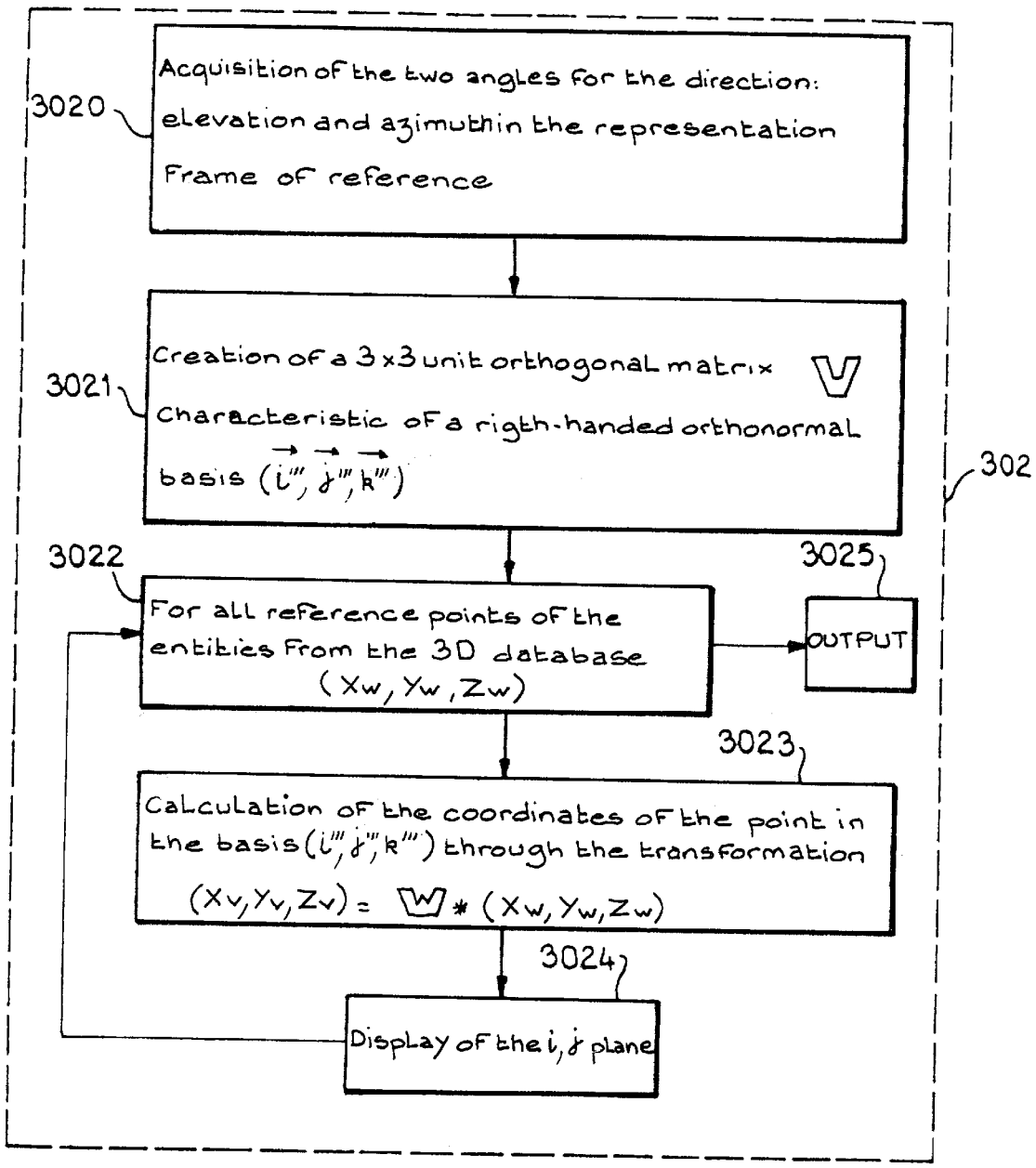
FIG_9b

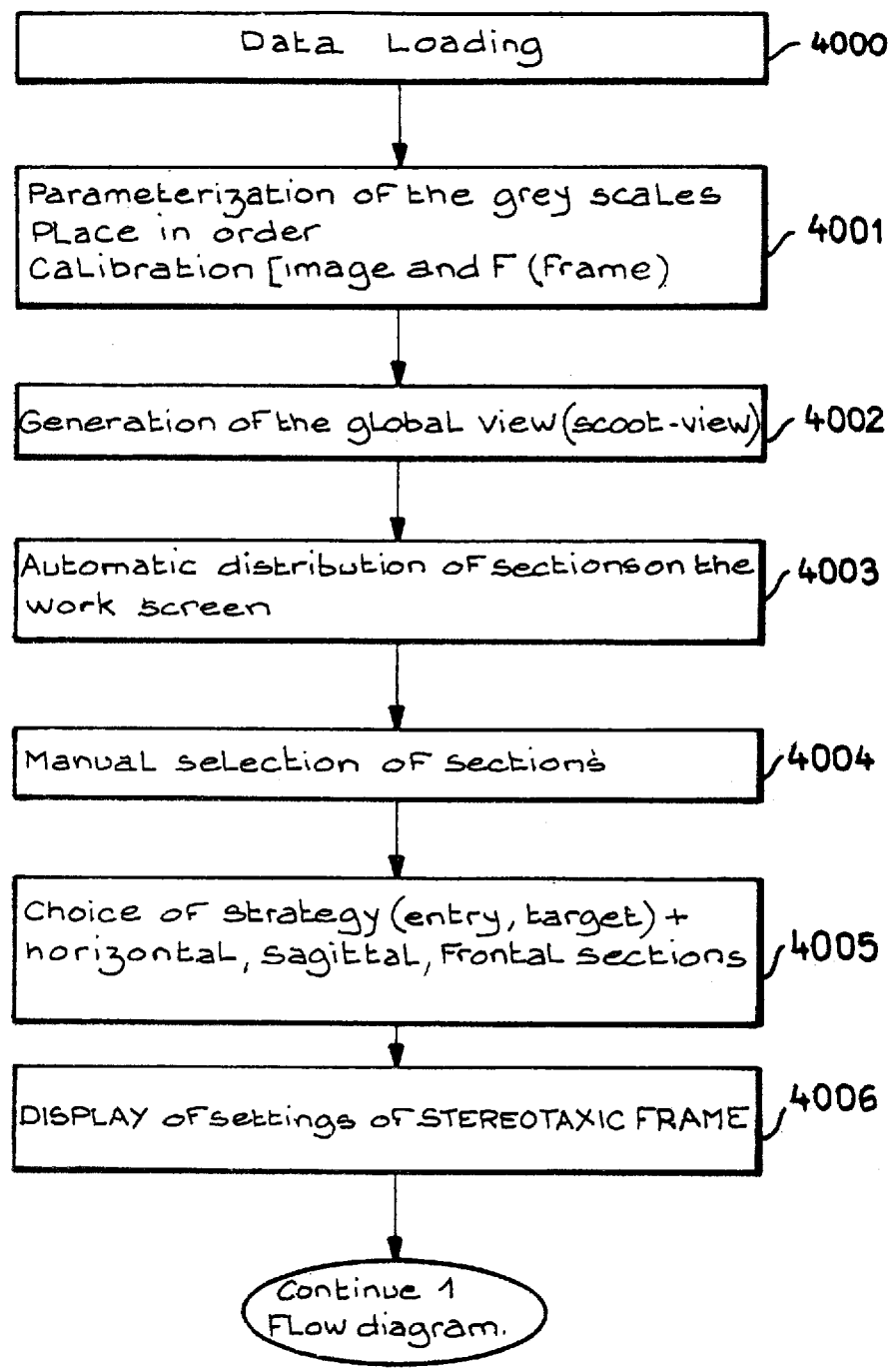
FIG_10a

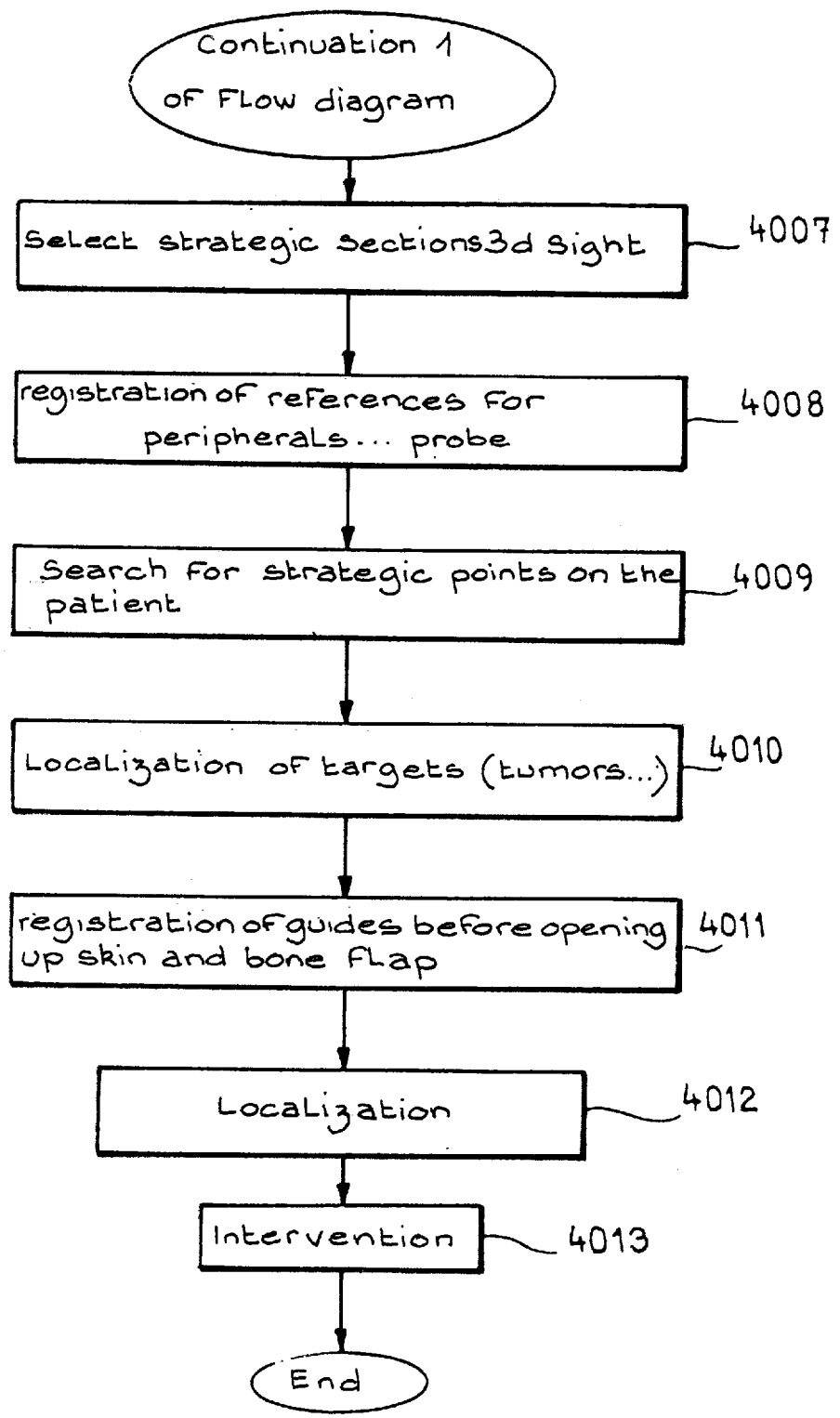
FIG_10b

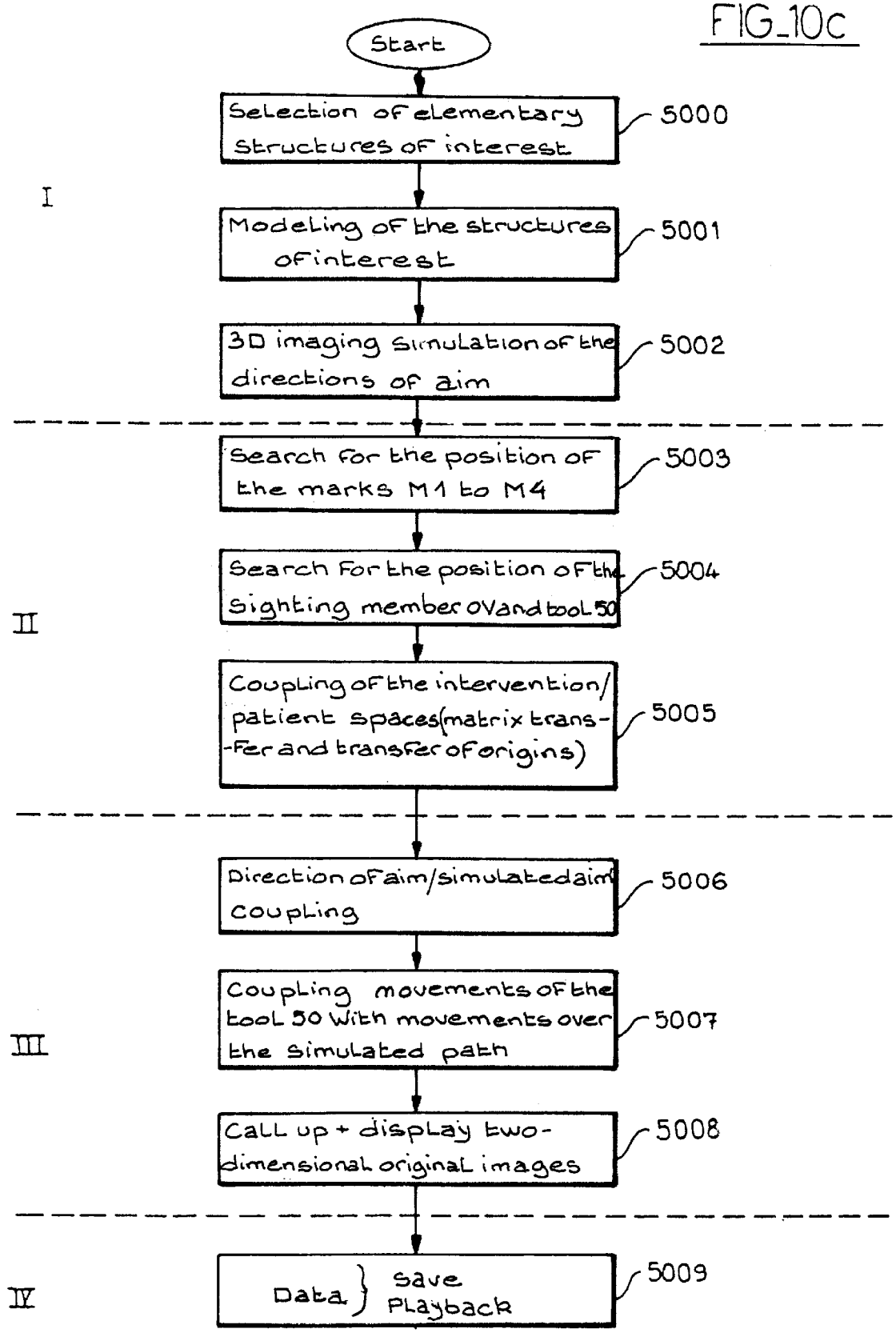

INTERACTIVE SYSTEM FOR LOCAL INTERVENTION INSIDE A NONHUMOGENEOUS STRUCTURE

The invention relates to an interactive system for local intervention inside a region of a nonhomogeneous structure.

The performing of local interventions inside a nonhomogeneous structure, such as intracranial surgical operations or orthopedic surgery currently poses the problem of optimizing the intervention path or paths so as to secure, on the one hand, total intervention over the region or structure of interest, such as a tumor to be treated or explored and, on the other hand, minimal lesion to the regions neighboring or adjoining the region of interest, this entailing the localizing and then the selecting of the regions of the nonhomogeneous structure which are least sensitive to being traversed or the least susceptible to damage as regards the integrity of the structure.

Numerous works aimed at providing a solution to the abovementioned problem have hitherto been the subject of publications. Among the latter may be cited the article entitled "Three Dimensional Digitizer (Neuronavigator): New Equipment for computed Tomography Guided Stereotaxic Surgery", published by Eiju Watanabe, M.D., Takashi Watanabe, M.D., Shinya Manaka, M.D., Yoshiaki Mayanagi, M.D., and Kintomo Takakura, M.D. Department of Neurosurgery, Faculty of Medicine, University of Tokyo, Japan, in the journal Surgery Neurol. 1987: 27 pp. 543–547, by Elsevier Science Publishing Co., Inc. The Patent WO-A-88 09151 teaches a similar item of equipment.

In the abovementioned publications are described in particular a system and an operational mode on the basis of which a three-dimensional position marking system, of the probe type, makes it possible to mark the three-dimensional position coordinates of a nonhomogeneous structure, such as the head of a patient having to undergo a neurosurgical intervention, and then to put into correspondence as a function of the relative position of the nonhomoc.eneous structure a series of corresponding images consisting of two-dimensional images sectioned along an arbitrary direction, and obtained previously with the aid of a medical imaging method of the "scanner" type.

The system and the operational mode mentioned above offer a sure advantage for the intervening surgeon since the latter has available, during the intervention, apart from a direct view of the intervention, at least one two-dimensional sectional view enabling him to be aware, in the sectional plane, of the state of performance of the intervention.

However, and by virtue of the very design of the system and of the operational mode mentioned above, the latter allow neither a precise representation of the state of performance of the intervention, nor partially or totally automated conduct of the intervention in accordance with a program for advance of the instrument determined prior to the intervention.

Such a system and such an operational mode cannot therefore claim to eradicate all man-made risk, since the intervention is still conducted by the surgeon alone.

The objective of the present invention is to remedy the whole of the problem cited earlier, and in particular to propose a system permitting as exact as possible a correlation, at any instant, between an intervention modeling on the screen and the actual intervention, and furthermore the representation from one or more viewing angles, and if appropriate in one or more sectional planes, of the nonhomogeneous structure, the sectional plane or planes possibly being for example perpendicular to the direction of the path of advance of the instrument or of the intervention tool.

Another objective of the present invention is also the implementation of a system permitting simulation of an optimal trajectory of advance of the tool, so as to constitute an assisted or fully programed intervention.

Finally, an objective of the present invention is to propose a system making it possible, on the basis of the simulated trajectory and of the programed intervention, to steer the movement of the instrument or tool to the said trajectory so as to carry out the programed intervention.

The invention proposes to this effect an interactive system for local intervention inside a region of a nonhomogeneous structure to which is tied a reference structure containing a plurality of base points, characterized in that it comprises:

means of dynamic display by three-dimensional imaging of a representation of the nonhomogeneous structure and of a reference structure tied to the nonhomogeneous structure, including images of the base points, means of delivering the coordinates of the images of the base points in the first reference frame, means of securing the position of the non-homogeneous structure and the reference structure with respect to a second reference frame.

marker means for delivering the coordinates of the base points in the second reference frame, means of intervention comprising an active member whose position is determined with respect to the second reference frame, means of optimizing the transfer of reference frames from the first reference frame to the second reference frame and vice versa, on the basis of the coordinates of the images of the base points in the first reference frame and of the coordinates of the base points in the second reference frame, in such a way as to reduce to a minimum the deviations between the coordinates of the images of the base points in the first reference frame and the coordinates of the base points, expressed in the said first reference frame with the aid of the said reference frame transfer tools, means for defining with respect to the first reference frame a simulated origin of intervention and a simulated direction of intervention, and reference frame transfer means using the said reference frame transfer tools to establish a bidirectional coupling between the simulated origin of intervention and the simulated direction of intervention and the position of the active member.

Figure 4:
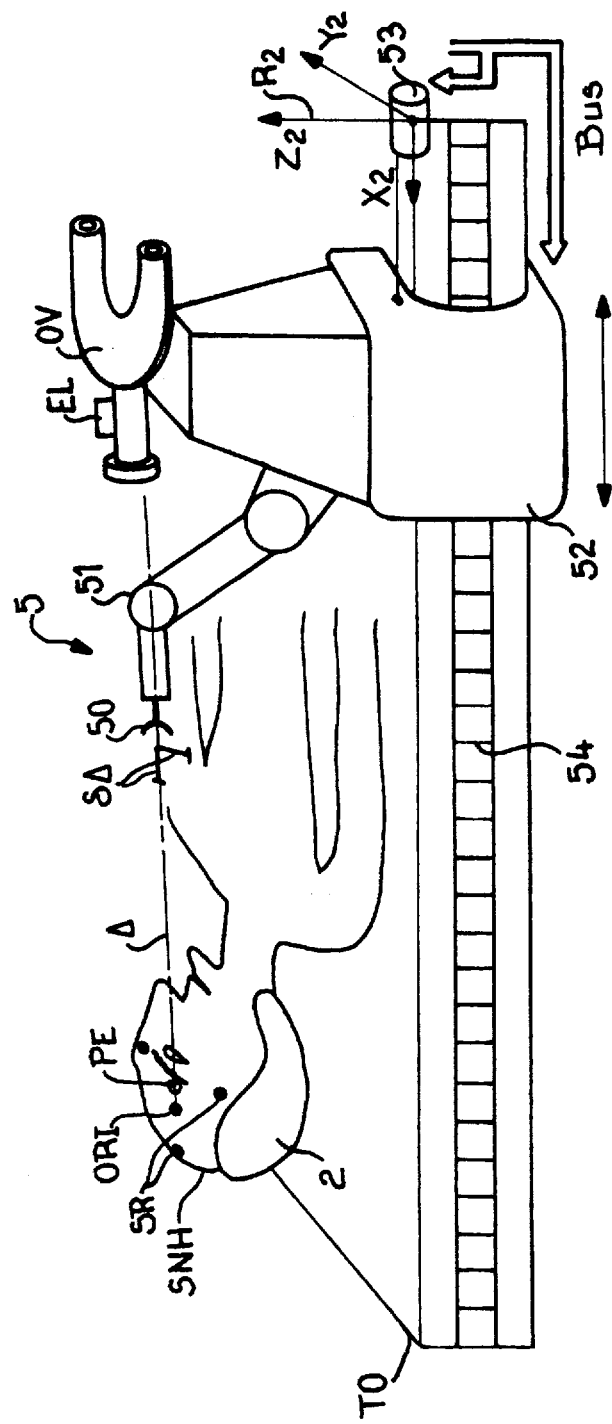
Figure 6:
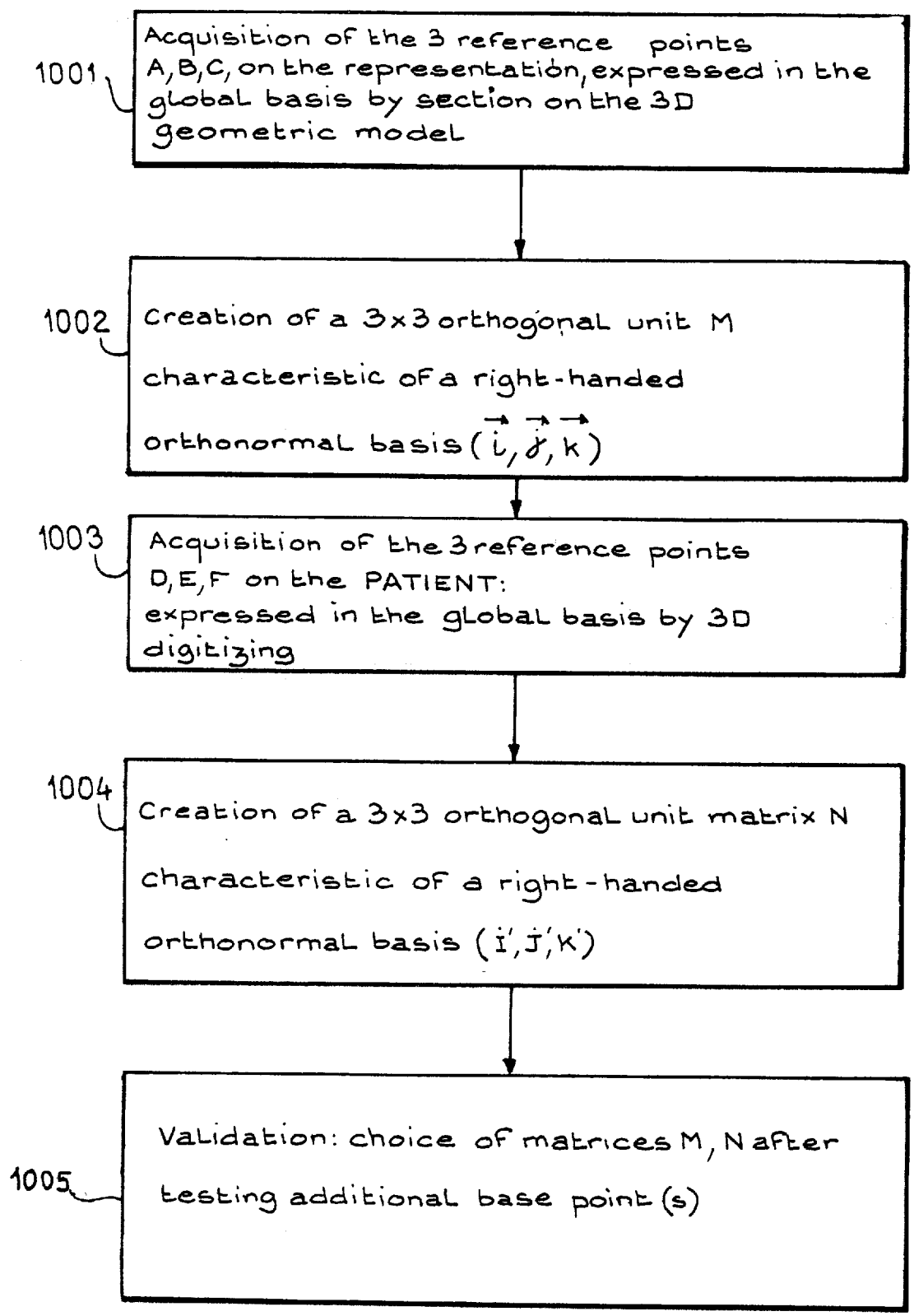

A more detailed description of the system of the invention will be given below with reference to the drawings in which:

FIG. 1 represents a general view of an interactive system for local intervention inside a region of a nonhomogeneous structure according to the present invention, FIG. 2 represents, in the case where the nonhomogeneous Structure consists of the head of a patient, and with a view to a neurosurgical intervention, a reference structure tied to the nonhomogeneous structure and enabling a correlation to be established between a "patient" reference frame and a reference frame of images of the patient which were made and stored previously, FIG. 3 represents an advantageous embodiment of the spacial distribution of the reference structure of FIG. 2, FIG. 4 preesents an advantageous embodiment of the intervention means set up on an operating table in the case of a neurosirgical intervention, FIGS. 5a and 5b represent a general flow diagram of functional steps implemented by the system, FIGS. 6 thru 8 represent flow diagrams of programs permitting implementation of certain functional steps of FIG. 5b, FIG. 9a represents a flow diagram of a program permitting implementation of a functional step of FIG. 5a, FIG. 9b represents a flow diagram of a program permitting implementation of another functional step of FIG. 5a, FIGS. 10a and 10b represent a general flow diagram of the successive steps of an interactive dialogue between the system of the present invention and the intervening surgeon and FIG. 10c represents a general flow diagram of the successive functional steps carried out by the system of the invention, having (sic) the intervention, prior to the intervention, during the intervention and after the intervention.

The interactive system for local intervention according to the invention will firstly be described in connection with FIG. 1.

A nonhomogeneous structure, denoted SNH, on which an intervention is to be performed, consists for example of the head of a patient in which a neurosurgical intervention is to be performed. It is however understood that the system of the invention can be used to carry out any type of intervention in any type of nonhomogeneous structure inside which structural and/or functional elements or units may be in evidence and whose integrity, during the intervention, is to be respected as far as possible.

The system comprises means, denoted 1, of dynamic display by three-dimensional imaging, with respect to a first reference frame $R_1$, of a representation (denoted RSR) of a reference structure SR (described later) tied to the structure SNH, and a representation or modeling of the nonhomogeneous structure, denoted RSNH.

More precisely, the means 1 make it possible to display a plurality of successive three-dimensional images, from different angles, of the representations RSNH and RSR.

The system of the invention also comprises means, denoted 2, of tied positioning, with respect to a second reference frame $R_2$, of the structures SNH and SR.

In the present non-limiting example, the head of the patient, bearing the reference structure SR, is fixed on an operating table TO to which are fixed the means 2 of tied positioning.

Of course, the patient whose head has been placed in the means 2 for tied positioning has previously been subjected to the customary preparations, in order to enable him to undergo the intervention.

The means 2 of the tied positioning with respect to $R_2$ will not be described in detail since they can consist of any means (such as a retaining headset) normally used in the field of surgery or neurosurgery. The reference frame $R_2$ can arbitrarily be defined as a tri-rectangular reference trihedron tied to the operating table TO, as represented in FIG. 1.

Means 3 of marking, with respect to the second reference frame $R_2$, the coordinates, denoted X2, Y2, Z2, of arbitrary points, and in particular of a certain number of base points of the reference structure SR are furthermore provided.

These base points constituting the reference structure SR can consist of certain notable points and/or of marks fixed to the patient, at positions selected by the surgeon and in particular at these notable points.

The system of the invention further comprises computing means 4 receiving means 3 of marking the coordinates X2, X2, Z2.

The computing means 4, as will be seen in detail later, are designed to elaborate optimal tools for reference frame transfer using on the one hand the coordinates in $R_2$, measured by the probe 3, of a plurality of base points of the structure SR, and on the other hand the coordinates in $R_1$, determined by graphical tools of the computer M01 (pointing by mouse, etc.), of the images of the corresponding base points in the representation RSR, so as to secure the best possible correlation between the information modeled in the computer equipment and the corresponding real-world information.

There is furthermore provision for reference frame transfer means 11 designed to use the tools thus elaborated and to secure this correlation in real time.

Moreover, means 40 are provided, as will be seen in detail later, for determining or modeling a reference origin of intervention ORI and a direction of intervention $\Delta$.

With the aid of the means 11, the modeled direction of intervention $\Delta$ can, at least prior to the intervention and at the start of the intervention, be materialized through an optical sighting system available to the surgeon, it being possible to steer this sighting system positionally with respect to the second reference frame $R_2$.

The sighting system will be described later.

The system of the present invention finally comprises means 5 of intervention comprising an active member, denoted 50, whose position is specified with respect to the second reference frame $R_2$. The active member can consist of the various tools used in surgical intervention. For example, in the case of an intercranial neurosurgical intervention, the active member could be a trephining tool, a needle, a laser or radioscope emission head, or an endoscopic viewing system.

According to an advantageous characteristic of the invention, by virtue of the reference frame transfer means 11, the position of the active member can be controlled dynamically on the basis of the prior modeling of the origin of intervention ORI and of the direction of intervention $\Delta$.

The means 1 of dynamic display by three-dimensional imaging of the representations RSNH and RSR comprise a file 10 of two-dimensional image data. The file 10 consists for example of digitized data from tomographic sections, from radiographs, from maps of the patient's head, and contained in an appropriate mass memory.

The successive tomographic sections can be produced prior to the intervention in a conventional manner, after the reference structure SR has been put in place on the nonhomogeneous structure SNH.

According to an advantageous feature, the reference structure SR can consist of a plurality of marks or notable points which can be both sensed by the marker means 3 and detected on the two-dimensional images obtained.

Of course, the abovementioned two-dimensional tomographic sections can likewise be produced by any medical imaging means such as a nuclear magnetic resonance system.

In a characteristic and well-known manner, each two-dimensional image corresponding to a tomographic scanner section corresponds to a structural slice thickness of about 2 to 3 mm, the pixels or image elements in the plane of the tomographic section being obtained with a precision of the order of ±1 mm. It is therefore understood that the marks or points constituting the reference structure SR appear on the images with a positional uncertainty, and an important feature of the invention will consist in minimizing these uncertainties as will be described later.

The system also comprises first means 110 for calculating and reconstructing three-dimensional images from the data from the file 10.

It also comprises a high-resolution screen 12 permitting the displaying of one or more three-dimensional or two-dimensional images constituting so many representations of the reference structure RSR and of the nonhomogeneous structure SNH.

Advantageously, the calculating means 110, the high-resolution screen and the mass memory containing the file 10 form part of a computer of the workstation type with conventional design and denoted MO1.

Preferably, the first calculating means 110 can consist of a CAD type program installed in the workstation MO1.

By way of non-limiting example, this program can be derived from the software marketed under the tradename "AUTOCAD" by the "AUTODESK" company in the United States of America.

Such software makes it possible, from the various digitized two-dimensional images, to reconstruct threedimensional images constituting the representations of the structures RSR and RSNH in arbitrary orientations.

Thus, as has furthermore been represented in FIG. 1, the calculating means 4 and 11 can consist of a third computer, denoted MO2 in FIG. 1.

The first and second computers MO1 and MO2 are interconnected by a conventional digital link (bus or network).

As a variant, the computers MO1 and MO2 can be replaced by a single workstation.

The marker means 3 consist of a three-dimensional probe equipped with a tactile tip 30.

This type of three-dimensional probe, known per se and not described in detail, consists of a plurality of hinged arms, marked in terms of position with respect to a base integral with the operating table TO. It makes it possible to ascertain the coordinates of the tactile tip 30 with respect to the origin $O_2$ of the reference frame $R_2$ with a precision better than 1 mm.

The probe is for example equipped with resolvers delivering signals representing the instantaneous position of the abovementioned tactile tip 30. The resolvers are themselves connected to the circuits for digital/analog conversion and sampling of the values representing these signals, these sampling circuits being interconnected in conventional manner to the second computer MO2 in order to supply it with the coordinates X2, X2, Z2 of the tactile tip 30.

As a variant or additionally, and as represented diagrammatically, the marker means 3 can comprise a set of video cameras 31 and 32 (or else infrared cameras) enabling pictures to be taken of the structures SNH and SR.

The set of cameras can act as a stereoscopic system permitting the positional plotting of the base points of the reference structure SR, or of other points of the nonhomogeneous structure SNH, with respect to the second reference frame $R_2$. The positional plotting can be done for example by appending a laser beam emission system making it possible to illuminate successively the points whose coordinates are sought, appropriate software making it possible to then determine the position of these points one by one with respect to $R_2$. This software will not be described since it can consist of position and shape recognition software normally available on the market.

According to another variant, the marker means 3 can comprise a telemetry system.

In this case, the marks of the structure SR can consist of small radiotransmitters implanted for example on the relevant points of the patient's head and designed to be visible on the two-dimensional images, appropriate electromagnetic or optical sensors (not shown) being provided in order to determine the coordinates of the said marks in the reference frame $R_2$ or in a reference frame tied to the latter.

It is important to note here that the general function of the base points of the reference structure is, on the one hand, to be individually localizable on the reference structure, in order to deduce from this the coordinates in $R_2$, and on the other hand, to be visualizable on the two-dimensional images so as to be identified (by their coordinates in $R_1$) and included in the representation RSR on the screen.

It can therefore involve special marks affixed at arbitrary points of the lateral surface of the structure SNH, or else at notable points of the latter, or else, when the notable points can in themselves be localized with high precision both on the structure SNH and on the 2D sections, notable points totally devoid of marks.

In FIG. 2 a plurality of marks, denoted M1 to Mi, these marks, in the case where the nonhomogeneous structure consists of the head of a patient, being localized for example between the eyebrows of the patient, on the latter's temples, and at the apex of the skull at a notable point such as the frontal median point.

More generally, for a substantially ovoid volume constituting the nonhomogeneous structure, there is advantageously provision for four base points at least on the outer surface of the volume.

Thus, as has been represented in FIG. 3, the four marks M1 to M4 of the reference structure are distributed so as preferably to define a more or less symmetric tetrahedron. The symmetry of the tetrahedron, represented in FIG. 3, is materialized by the vertical symmetry plane PV and the horizontal symmetry plane PH.

According to an advantageous characteristic, as will be seen later, the means of elaborating the reference frame transfer tools are designed to select three points of the tetrahedron which will define the "best plane" for the reference frame transfer.

Also, the presence of four or more points enables the additional point(s) to validate a specified selection.

More precisely, the presence of a minimum of four base points on the reference structure makes it possible to search for the minimum distortion between the points captured on the patient by the marker means consisting for example of the three-dimensional probe and the images of these points on the representation by three-dimensional imaging, the coordinates of which are calculated during processing. The best plane of the tetrahedron described earlier, that is to say the plane for which the uncertainty in the coordinates of the points between the points actually captured by the three-dimensional probe and the points of the representation of the reference structure RSR, is minimal, then becomes the reference plane for the reference frame transfer. Thus, the best correlation will be established between a modeled direction of intervention and a modeled origin of intervention, on the one hand, and the action of the member 50. Preferably, the origin of intervention will be placed at the center of the region in which the intervention is to be carried out, that is to say a tumor observed or treated for example.

Furthermore, it will be possible to take the noted residual uncertainty into account in order to effect the representation of the model and of the tools on the dynamic display means.

A more detailed description of the means of intervention 5 will now be given in connection with FIG. 4.

Preferably, the means of intervention 5 comprise a carriage 52 which is translationally mobile along the operating table TO, for example on a rack, denoted 54, whilst being driven by a motor, not shown, itself controlled by the computer MO2 for example, via an appropriate link. This movement system will not be described in detail since it corresponds to a conventional movement system available on the market. As a variant, the carriage 52 can be mobile over a distinct path separated from the operating table TO, or immobile with respect to the operating table and then constitute a support.

The support carriage 52 comprises in the first place a sighting member OV, constituting the above-mentioned sighting system, which can consist of a binocular telescope.

The sighting member OV enables the surgeon, prior to the actual intervention, or during the latter, to sight the presumed position of the region in which the intervention is to be carried out.

Furthermore, and in a non-limiting manner, with the sighting member OV can be associated a helium-neon laser emission system, denoted EL, making it possible to secure the aiming of a fine positioning or sighting laser beam on the structure SNH and in particular, as will be seen in detail later, to indicate to the surgeon the position of an entry point PE prior to the intervention, to enable the latter to open the skull at the appropriate location, and likewise to indicate to him what the direction of intervention will be. Additionally, the illuminating of the relevant point of the nonhomogeneous structure or at the very least the lateral surface of the latter enables the video cameras 31 and 32 to carry out, if necessary, a positional plotting.

Preferably, a system for measuring position by telemetry 53 is provided to secure the precise measurement of the position of the support carriage 52 of the sighting member OV and of the laser emission system EL. During the operation, and in order to secure the intervention, the carriage 52 can be moved along the rack 54, the position of the carriage 52 being measured very precisely by means of the system 53. The telemetry system 53 is interconnected with the microcomputer MO2 by an appropriate link.

The means of intervention 5 can advantageously consist of a guide arm 51 for the active member 50.

The guide arm 51 can advantageously consist of several hinged segments, each hinge being equipped with motors and resolvers making it possible to secure control of movement of the end of the support arm and the positional plotting of this same end and therefore of the active member 50 according to six degrees of freedom with respect to the carriage 52. The six degrees of freedom comprise, of course, three translational degrees of freedom with respect to a reference frame tied to the carriage 52 and three rotational degrees of freedom along these same axes.

Thus, the support arm 51 and the member 50 are marked in terms of instantaneous position with respect to the second reference frame $R_2$, on the one hand by way of the positional plot of the mobile carriage 52 and, on the other hand, by way of the resolvers associated with each hinge of the support arm 51.

In the case of an intracranial neurosurgical surgical intervention, the active member 50 can be removed and can consist of a trephining tool, a needle or radioactive or chemical implant, a laser or radioisotope emission head or an endoscopic viewing system. These various members will not be described since they correspond to instruments normally used in neurosurgery.

The materializing of the modeled direction of intervention can be effective by means of the laser emitter EL. This sighting being performed, the guide arm 51 can then be brought manually or in steered manner into superposition with the direction of intervention Δ.

In the case of manual positioning, the resolvers associated with the sighting member OV and the laser emitter EL, if appropriate, make it possible to record the path of the sighting direction, constituting in particular the actual direction of intervention, on the representation of the nonhomogeneous structure in the dynamic display means 1.

Furthermore, as will be described later and in preferential manner, the intervening surgeon will be able firstly to define a simulated intervention path and steer thereto the movements of the active member 50 in the nonhomogeneous structure in order effectively to secure all or part of the intervention.

In this case, the progress of the intervention tool 50 is then steered directly to the simulated path (data ORI, Δ) by involving the reference frame transfer means 11 in order to express the path in the reference frame $R_2$.

A more detailed description of the implementation of the operational mode of the system of the invention will now be described in connection with FIGS. 5a and 5b.

According to FIG. 5a, the first step consists in obtaining and organizing in memory the two-dimensional image data (step 100). Firstly, the nonhomogeneous structure SNH is prepared. In the case of a neurosurgical intervention for example, this means that the patient's head can be equipped with marks constituting the base points of the reference structure SR. These marks can be produced by means of points consisting of a dye partially absorbing the X-rays, such as a radiopaque dye.

The abovementioned marks are implanted by the surgeon on the patient's head at notable points of the latter [sic], and images can then be taken of the nonhomogeneous structure SNH by tomography for example, by means of an apparatus of the X-ray scanner type.

This operation will not be described in detail since it corresponds to conventional operations in the field of medical imaging.

The two-dimensional image data obtained are then constituted as digitized data in the file 10, these data being themselves marked with respect to the reference frame $R_1$ and making it possible, on demand, to restore the two-dimensional images onto the dynamic display means 1, these images representing superimposed sections of the nonhomogeneous structure SNH.

From the digitized image data available to the surgeon, the latter then proceeds, as indicated at 101 in FIG. 5a, to select the structures of interest of the abovementioned images.

The purpose of this step is to facilitate the work of the surgeon by forming three-dimensional images which contain only the contours of the elements of the structure which are essential for geometrical definition and real-time monitoring of the progress of the intervention.

In the case where the nonhomogeneous structure SNH consists of the head of a patient, an analysis of the two-dimensional image data makes it possible, from values of optical density of the corresponding image-points, straightaway to extract the contours of the skull, to check the distance scales, etc.

Preferably, the abovementioned operations are performed on a rectangle of interest for a given two-dimensional image, this making it possible, by moving the rectangle of interest, to cover the whole of the image.

The above analysis is performed by means of suitable software which thus makes it possible to extract and vectorize the contours of the structures which will be modeled in the representations RSNH and RSR.

The structures modeled in the case of a neurosurgical intervention are for example the skull, the cerebral ventricles, the tumor to be observed or treated, the falx cerebri, and the various functional regions.

According to a feature of the interactive system of the invention, the surgeon may have available a digitizing table or other graphics peripheral making it possible, for each displayed two-dimensional image, to rectify or complete the definition of the contour of a particular region of interest.

It will be noted finally that by superimposing the extracted contours on the displayed two-dimensional image, the surgeon will be able to validate the extractions carried out.

The extracted contours are next processed by sampling points to obtain their coordinates in the reference frame $R_1$, it being possible to constitute these coordinates as an ASCII type file. This involves step 102 for generating the three-dimensional data base.

This step is followed by a step 103 of reconstructing the three-dimensional model. This step consists firstly, with the aid of the CAD type software, in carrying out on the basis of the contours of the structures of interest constituted as vectorized two-dimensional images an extrapolation between the various sectional planes.

The abovementioned extrapolation is carried out preferably by means of a "B-spline" type algorithm which seems best suited. This extrapolation transforms a discrete item of information, namely the successive sections obtained by means of the scanner analysis, into a continuous model permitting three-dimensional representation of the volume envelopes of the structures.

It should be noted that the reconstruction of the volumes constituting the structures of interest introduces an approximation related in particular to the spacing and non-zero thickness of the acquisition sections. An important characteristic of the invention, as explained in detail elsewhere, is on the one hand to minimize the resulting uncertainties in the patient-model correlation, and on the other hand to take into account the residual uncertainties.

The CAD type software used possesses standard functions which enable the model to be manipulated in space by displaying it from different viewpoints through just a criterion defined by the surgeon (step 104).

The software can also reconstruct sectional representation planes of the nonhomogeneous structure which differ from the planes of the images from the file 10, this making it possible in particular to develop knowledge enhancing the data for the representation by building up a neuro-anatomical map.

The surgeon can next (step 105) determine a model of intervention strategy taking into account the modeled structures of interest, by evaluating the distance and angle ratios on the two-and three-dimensional representations displayed.

This intervention strategy will consist, in actual fact, on the one hand in localizing the tumor and in associating therewith a "target point", which will subsequently be able to substitute for the origin common to all the objects (real and images) treated by the system, and on the other hand in determining a simulated intervention path respecting to the maximum the integrity of the structures of interest. This step can be carried out "in the office", involving only the workstation.

Once this operation is performed and prior to the intervention, the following phase consists in implementing the steps required to establish as exact as possible a correlation between the structure SNH (real world) and the representation RSNH (computer world). This involves steps 106 to 109 of FIG. 5b.

Firstly, as represented in FIG. 5b at step 107, marking of the base points of the reference structure SR with respect to the second reference frame is carried out with the aid of the marker means 3, by delivering to the system the coordinates X2, Y2, Z2 of the said base points.

The following step 106 consists in identifying on the representations RSNH and RSR displayed on the screen the images of the base points which have just been marked. More precisely, with the aid of appropriate graphics peripherals, these representations (images) of the base points are selected one by one, the workstation supplying on each occasion (in this instance to the computer MO2) the coordinates of these points represented in the reference frame $R_1$.

Thus the computer MO2 has available a first set of three-dimensional coordinates representing the position of the base points in $R_2$, and a second set of three-dimensional coordinates representing the position of the representations of the base points in $R_1$.

According to an essential feature of the invention, these data will be used to elaborate at 108, 109, tools for reference frame transfer (from $R_1$ to $R_2$ and vice versa) by calling upon an intermediate reference frame determined from the base points and constituting an intermediate reference frame specific to the reconstructed model.

More precisely, the intermediate reference frame is constructed from three base points selected so that, in this reference frame, the coordinates of the other base points after transfer from $R_2$ and the coordinates of the representations of these other base points after transfer from $R_1$ are expressed with the greatest consistency and minimum distortion.

When the step of elaborating the reference frame transfer tools is concluded, these tools can be used by he system to secure optimal coupling between the real world and the computer world (step 1110).

Furthermore, according to a subsidiary feature of the present invention, the system can create on the display means a representation of the nonhomogeneous structure and of the intervention member which takes account of the deviations and distortions remaining after the "best" reference frame transfer tools have been selected (residual uncertainties). More precisely, from these deviations can be deduced by the calculating means a standard error likely to appear in the mutual positioning between the representation of the nonhomogeneous structure and the representation of elements (tools, sighting axes, etc.) referenced on $R_2$ when using the reference frame transfer tools. This residual uncertainty, which may in practice be given substance through an error matrix, can be used for example to represent certain contours (tool, structures of interest to be avoided during the intervention, etc.) with dimensions larger than those which would normally be represented starting from the three-dimensional data base or with the aid of coordinates marked in $R_2$, the said larger dimensions being deduced from the "normal" dimensions by involving the error matrix. For example, if the member were represented normally, in transverse section, by a circle of diameter D1, a circle of diameter D2>D1 can be represented in substance, with the difference D2-D1 deduced from the standard error value. In this way, when a direction of intervention will be selected making it possible to avoid traversing certain structures of interest, the taking into account of an "enlarged" size of the intervention tool will eradicate any risk of the member, because of the abovementioned errors, accidently traversing these structures.

Back at step 105, and as will be seen in more detail with reference to FIGS. 9a and 9b, the reference origin of intervention ORI and the direction of intervention Δ, that is to say the simulated intervention path, can be determined according to various procedures.

According to a first procedure, the trajectory can be defined from two points, namely an entry point PE (FIG. 3)

and a target point, that is to say substantially the center of the structure of interest consisting of the tumor to be observed or treated. Initially, these two points are localized on the model represented on the screen.

According to a second methodology, the trajectory can be determined from the abovementioned target point and from a direction which takes account of the types of structures of interest and of their positions with a view to optimally respecting their integrity.

After the abovementioned step 108, the surgeon can at step 1110 perform the actual intervention.

The intervention can advantageously be performed by steering the tool or active member over the simulated intervention path, determined in step 1110.

As a variant, given that the support arm 51 for the active member, equipped with its resolvers, continuously delivers the coordinates in $R_2$ of the said active member to the system, it is also possible to perform the operation manually or semi-manually, by monitoring on the screen the position and motions of a representation of the tool and by comparing them with the simulated, displayed intervention path.

It will furthermore be noted that the modeled direction of intervention can be materialized with the aid of the laser beam described earlier, the positioning of the latter (with respect to $R_2$) being likewise carried out by virtue of the reference frame transfer tools.

Certain functional features of the system of the invention will now be described in further detail with reference to FIGS. 6, 7, 8, 9a and 9b.

The module for elaborating the reference frame transfer tools (steps 108, 109 of FIG. 5b) will firstly be described with reference to FIG. 6.

This module comprises a first sub-module 1001 for acquiring three points A, B, C, the images of the base points of SR on the representation RSNH (the coordinates of these points being expressed in the computer reference frame $R_1$), by successive selections of these points on the representation. To this effect, the surgeon is led, by means of a graphics interface such as a "mouse" to point successively at the three selected points A, B, C.

The module for preparing the transfer tools also comprises a second sub-module, denoted 1002, for creating a unit three-dimensional orthogonal matrix M, this matrix being characteristic of a right-handed orthonormal basis represented by three unit vectors $\vec{i}$, $\vec{j}$, $\vec{k}$, which define an intermediate reference frame tied to $R_1$.

The unit vectors $\vec{i}$, $\vec{j}$ and $\vec{k}$ are given by the relations:

$$\vec{j} = \vec{AB}/\|AB\|$$

$$\vec{k} = \left(\vec{BA} \wedge \vec{BC}\right)/\|\vec{BA} \wedge \vec{BC}\|$$

$$\vec{i} = \vec{j} \wedge \vec{k}$$

where $\| \|$ designates the norm of the relevant vector.

In the above relations, the sign "$\wedge$" designates the vector product of the relevant vectors.

Similarly, the module for preparing the transfer tools comprises a third sub-module, denoted 1003, for acquiring three base points D, E, F, of the structure SR, these three points being those whose images on the model are the points A, B, C respectively. For this purpose, the surgeon, for example by means of the tactile tip 30, successively senses these three points to obtain their coordinates in $R_2$.

The sub-module 1003 is itself followed, as represented in FIG. 6, by a fourth sub-module 1004 for creating a unit three-dimensional orthogonal matrix N, characteristic of a right-handed orthonormal basis comprising three unit vectors $\vec{i}'$, $\vec{j}'$, $\vec{k}'$ and which is tied to the second reference frame $R_2$ owing to the fact that the nonhomogeneous structure SNH is positionally tied with respect to this reference frame.

The three unit vectors $\vec{i}'$, $\vec{j}'$, $\vec{k}'$ are defined by the relations:

$$\vec{j}' = \vec{DE}/\|\vec{DE}\|$$

$$\vec{k}' = \left(\vec{ED} \wedge \vec{EF}\right)/\|\vec{ED} \wedge \vec{EF}\|$$

$$\vec{i}' = \vec{j}' \wedge \vec{k}'$$

As indicated above, to the extent that the base points of the reference structure can be marked in $R_2$ with high precision, so their representation in the computer base $R_1$ is marked with a certain margin of error given on the one hand the non-zero thickness (typically from 2 to 3 mm) of the slices represented by the two-dimensional images from the file 10, and on the other hand (in general to a lesser extent) the definition of each image element or pixel of a section.

According to the invention, once a pair of transfer matrices M, N has been elaborated with selected points A, B, C, D, E, F, it is sought to validate this selection by using one or more additional base points; more precisely, for the or each additional base point, this point is marked in $R_2$ with the aid of the probe 30, the representation of this point is marked in $R_1$ after selection on the screen, and then the matrices N and M are applied respectively to the coordinates obtained, in order to obtain their expressions in the bases ($\vec{i}'$, $\vec{j}'$, $\vec{k}'$) and ($\vec{i}$, $\vec{j}$, $\vec{k}$) respectively. If these expressions are in good agreement, these two bases can be regarded as a single intermediate reference frame, this securing the exact as possible mathematical coupling between the computer reference frame $R_1$ tied to the model and the "real" reference frame $R_2$ tied to the patient.

In practice, the module for elaborating the reference frame transfer tools can be designed to perform steps 1001 to 1004 in succession on basic triples which differ on each occasion (for example, if four base points have been defined associated with four representations in RSR, there are four possible triples), in order to perform the validation step 1005 for each of these selections and finally in order to choose the triple for which the best validation is obtained, that is to say for which the deviation between the abovementioned expressions is smallest. This triple defines the "best plane" mentioned elsewhere in the description, and results in the "best" transfer matrices M and N.

As a variant, it will be possible for the selection of the best plane to be made at least in part by the surgeon by virtue of his experience.

It should be noted that the reference frame transfer will only be concluded by supplementing the matrix calculation with the matrices M, N with a transfer of origin, so as to create a new common origin for example at the center of the tumor to be observed or treated (point ORI). This transfer of origin is effected simply by appropriate subtraction of vectors on the one hand on the coordinates in $R_1$, and on the other hand on the coordinates in $R_2$. These vectors to be subtracted are determined after localization of the center of the tumor on the representation.

Furthermore, the means described above for establishing the coupling between the patient's world and the model's world can also be used to couple to the model's world that of map data, also stored in the workstation and expressed in a different reference frame denoted $R_3$. In this case, since these data contain no specific visible mark, the earlier described elaboration of matrices is performed by substituting for these marks the positions of notable points of the patient's head. These may be temporal points, the frontal median point, the apex of the skull, the center of gravity of the orbits of the eyes, etc.

The corresponding points of the model can be obtained either by selection by mouse or graphics tablet on the model, or by sensing on the patient himself and then using the transfer matrices.

The above step of elaborating the reference frame transfer tools, conducted in practice by the calculating means 4, makes it possible subsequently to implement the reference frame transfer means (FIGS. 7 and 8).

With reference to FIG. 7, the first transfer sub-module 201 comprises a procedure denoted 2010 for aquiring the coordinates XM, YM, ZM, expressed in $R_1$, of the point to be transferred, by selecting on the representation.

The procedure 2010 followed by a procedure 2011 for calculating the coordinates XP, YP, ZP (expressed in $R_2$) of the corresponding real point on the patient through the transformation:

{XP, YP, ZP}=M*$N^{-1}$*{XM, YM, ZM} where M * $N^{-1}$ represents the product of the matrix M and the inverse matrix N.

The procedure 2011 is followed by a processing procedure 2012 utilizing the calculated coordinates XP, YP, ZP, for example to indicate the corresponding point on the surface of the structure SNH by means of the laser emission system EL, or again to secure the intervention at the relevant point with coordinates XP, YP, ZP (by steering the active member).

Conversely, in order to secure a transfer from SNH to RSNH, the second sub-module 202 comprises (FIG. 8) a procedure denoted 2020 for acquiring on the structure SNH the coordinates XP, YP, ZP (expressed in $R_2$) of a point to be transferred.

These coordinates can be obtained by means of the tactile tip 30 for example. The procedure 2020 is followed by a procedure 2021 for calculating the corresponding coordinates XM, YM, ZM in $R_1$ through the transformation:

{XM, YM, ZM}=N*$M^{-1}$*{XP, YP, ZP}

A procedure 2022 next makes it possible to effect the displaying of the point with coordinates XM, YM, ZM on the model or again of a straight line or of a plane passing through this point and furthermore meeting other criteria.

It will be noted here that the two sub-modules 201, 202 can used [sic] by the surgeon at any moment for the purpose of checking the valid nature of the transfer tools; in particular, it is possible to check at any time that a real base point, with coordinates known both in $R_2$ and $R_1$ (for example a base point of SR or an arbitrary notable point of the structure SNH visible on the images), correctly relocates with respect to its image after transferring the coordinates in step 2011.

In the event of an excessive difference, a new step of elaboration of the transfer tools is performed.

Furthermore, the sub-modules 201, 202 can be designed to also integrate the taking into account of the residual uncertainty, as spoken of above, so as for example to represent on the screen a point sensed not in a pointwise manner, but in the form for example of a circle or a sphere representing the said uncertainty.

From a simulated intervention path, for example on the representation RSNH, or from any other straight line selected by the surgeon, the invention furthermore enables the model to be represented on the screen from a viewpoint corresponding to this straight line. Thus the third transfer subroutine comprises, as represented in FIGS. 9a and 9b, a first module 301 for visualizing the representation in a direction given by two points and a second module 302 for visualizing the representation in a direction given by an angle of elevation and an angle of azimuth.

The first module 301 for visualizing the representation in a direction given by two points comprises a first sub-module denoted 3010 permitting acquisition of the two relevant points which will define the selected direction. The coordinates of these points are expressed in the reference frame $R_1$, these points having either been acquired previously on the nonhomogeneous structure SNH for example by means of the tactile tip 30 and then subjected to the reference frame transfer, or chosen directly on the representation by means of the graphics interface of the "mouse" type.

The first sub-module 3010 is followed by a second sub-module denoted 3011 permitting the creation of a unit, orthogonal three-dimensional matrix V characteristic of a right-handed orthonormal basis $\vec{i}''$, $\vec{j}''$, $\vec{k}''$ the unit vectors $\vec{i}''$, $\vec{j}''$, $\vec{k}''$, being determined through the relations:

$$\vec{k}'' = \vec{AB}/\|\vec{AB}\|;$$
$$\vec{i}'' \cdot \vec{k}'' = 0; \vec{i}'' \cdot \vec{z}'' = 0; \|\vec{i}''\| = 1;$$
$$\vec{j}'' = \vec{k}'' \wedge \vec{i}''$$

where "Λ" represents the vector product and "." symbolizes the scalar product.

The sub-module 3011 is followed by a routine 3012 making it possible to secure for all the points of the entities (structures of interest) of the three-dimensional data base of coordinates XW, YW, ZW in $R_1$ a conversion into the orthonormal basis ($\vec{i}''$, $\vec{j}''$, $\vec{k}''$) by the relation:

{XV, YV, ZV}=V*{XW, YW, ZW}

The subroutine 3013 is then followed by a subroutine 3014 for displaying the plane i'', j'', the subroutines 3013 and 3014 being called up for all the points, as symbolized by the arrow returning to block 3012 in FIG. 9a.

When all the points have been processed, an output module 3015 permits return to a general module, which will be described later in the description. It is understood that this module enables two-dimensional images to be reconstructed in planes perpendicular to the direction defined by A and B.

In the same way, the second module 302 (FIG. 9b) for visualizing the representation from a viewpoint given by an angle of elevation and an angle of azimuth comprises a first sub-module 3020 for acquiring the two angles in the representation frame of reference.

The selection of the angles of elevation and of azimuth can be made by selecting from a predefined data base or by moving software cursers associated with each view or else by modification relative to a current direction, such as the modeled direction of intervention. The sub-module 3020 is itself followed by a second sub-module 3021 for creating a unit orthoganal three-dimensional matrix W characteristic of a right-handed orthonormal basis of unit vectors $\vec{i}'''$, $\vec{j}'''$, $\vec{k}'''$. They are defined by the relations:

$$\vec{i}''' \cdot \vec{k}''' = O;$$

$$\vec{k}''' \cdot \vec{z}''' = \sin(\text{azimuth})$$

$$\vec{j}''' \cdot \vec{z}''' = O;$$

$$\vec{i}''' \cdot \vec{y} = \cos(\text{elevation});$$

$$\vec{i}''' \cdot \vec{x}''' = \sin(\text{elevation})$$

$$\vec{j}''' = \vec{k}''' \wedge \vec{i}'''$$

A routine 3022 is then called for all the points of the entities of the three-dimensional data base of coordinates XW, YW, ZW and enables a first sub-routine 3023 to be called permitting calculation of the coordinates of the relevant point in the right-handed orthonormal bases $\vec{i}'''$, $\vec{j}'''$ $\vec{k}'''$ through the transformation:

{XV, YV, ZV}=V*{XW, YW, ZW}

The sub-routine 3023 is itself followed by a sub-routine 3024 for displaying the plane i''', j''', the two sub-routines 3023 and 3024 then being called up for each point as symbolized by the return via the arrow to the block 3022 for calling the abovementioned routine. When all the points have been processed, an output sub-module 3025 permits a return to the general menu.

Of course, all of the programs, sub-routines, modules, sub-modules and routines destroyed earlier are managed by a general "menu" type program so as to permit interactive driving of the system by screen dialogue with the intervening surgeon by specific screen pages.

A more specific description of a general flow diagram illustrating this general program will now be given in connection with FIGS. 10a and 10b.

Thus, in FIG. 10a has been represented in succession a screen page 4000 relating to the loading of data from the digitized file 10, followed by a screen page 4001 making it possible to secure the parameterizing of the grey scales of the display on the dynamic display means 1 and to calibrate the image, for example.

The screen page 4001 is followed by a screen page 4002 making it possible to effect the generation of a global view and then a step or screen page 4003 makes it possible to effect an automatic distribution of the sections on the screen of the workstation.

A screen page 4004 makes it possible to effect a manual selection of sections and then a screen page 4005 makes it possible to effect the selection of the strategy (search for the entry points and for the possible directions of intervention, first localizing of the target (tumor . . . ) to be treated . . . ), as defined earlier, and to select the position and horizontal, sagittal and frontal distribution of the sections.

A screen page 4006 also makes it possible to effect a display of the settings of a possible stereotaxic frame.

It will be recalled that the reference structure SR advantageously replaces the stereotaxic frame formerly used to effect the marking of position inside the patient's skull.

There may furthermore be provided a screen-page 4007 for choosing strategic sections by three-dimensional viewing, on selection by the surgeon, and then at 4008 the aligning of the references of the peripherals (tool, sighting members, etc., with the aid of the probe 30.

A screen page 4009 is also provided to effect the search for the base points on the patient with the aid of the said probe, following which the steps of construction of the reference frame transfer tools and of actual reference frame transfer are performed, preferably in a user-transparent manner.

Another screen page 4010 is then provided, so as to effect the localizing of the target on the representation (for example a tumor to be observed or treated in the case of a neurosurgical intervention) in order subsequently to determine a simulated intervention path.

Then a new screen page 4011 makes it possible to effect the setting of the guides for the tool on the basis of this simulated path before opening up the skin and bone flaps on the patient's skull.

Then a new localizing step 4012 makes it possible to check whether the position of the guides corresponds correctly to the simulated intervention path.

The screen page 4012 is followed by a so-called intervention screen page, the intervention being performed in accordance with step 1110 of FIG. 5b.

A more detailed description of the interactive dialogue between the surgeon and the system during a surgical, and in particular a neurosurgical, intervention will follow with reference to FIG. 10c and to all of the preceding description.

The steps of FIG. 10c are also integrated in the general program mentioned earlier; there are undertaken in succession a first phase I (preparation of the intervention), then a second phase II, (prior to the actual intervention, the patient is placed in a condition for intervention, the reference structure SR being tied to the second reference frame $R_2$), then a third phase III (intervention) and finally a post-intervention phase IV.

With a view to preparing the intervention, the system requests the surgeon (step 5000) to choose the elementary structures of interest (for example bones of the skull, ventricles, vascular regions, the tumor to be explored or treated, and the images of the marks constituting in the first reference frame the representation RSR).

The choice of the elementary structures of interest is made on the display of the tomographic images, for example, called up from the digitized file 10.

The system next performs, at step 5001, a modeling of the structures of interest, as described earlier. Then, the nonhomogeneous structure having been thus constituted as a three-dimensional model RSNH displayed on the screen, the intervening surgeon is then led to perform a simulation by three-dimensional imaging, at step 5002, with a view to defining the intervention path of the tool 50.

During phase II the patient being placed in a condition for intervention and his head and the reference structure SR being tied to the second reference frame $R_2$, the surgeon performs at step 5003 a search for the position of the marks M1 to M4 constituting base points of the reference structure in the second reference frame $R_2$, and then during a step 5004, performs a search for the position of the sighting systems, visualizing member OV, or of the tools and intervention instruments 50, still in the second reference frame $R_2$, so as, if appropriate, to align these implements with respect to $R_2$.

The system then performs the validation of the intervention/patient spaces and representation by three-dimensional imaging in order to determine next the common origin of intervention ORI. In other words, the matrix reference frame transfer described above is supplemented with the necessary origin translations (origins 01 and 02 aligned on ORI).

This operation is performed as described earlier.

Phase III corresponds to the intervention, during which the system effects at step 5006 a permanent coupling in real time between the direction of aim of the active member 50, and/or of the direction of aim of the sighting member OV (and if appropriate of the laser beam), with the direction of aim (of observation) simulated by three-dimensional imaging on the display means 1, and vice versa.

In the following step 5007, the coupling is effected of the movements and motions of the intervention instrument with their movements simulated by three-dimensional imaging, with automatic or manual conduct of the intervention.

As noted at 5008, the surgeon can be supplied with a permanent display of the original two-dimensional sectional images in planes specified with respect to the origin ORI and to the direction of intervention. Such a display enables the surgeon at any time to follow the progress of the intervention in real time and to be assured that the intervention is proceeding in accordance with the simulated intervention. In phase IV which is executed after the intervention, the system effects a saving of the data acquired during the intervention, this saving making it possible subsequently to effect a comparison in real time or deferred in the event of successive interventions on the same patient.

Furthermore, the saved data make it possible to effect a playback of the operations carried out with the option of detailing and supplementing the regions traversed by the active member 50.

Thus, a particularly powerful interactive system for local intervention has been described.

Thus, the system which is the subject of the present invention makes it possible to represent a model containing only the essential structures of the nonhomogeneous structure, this facilitating the work of preparation and of monitoring of the intervention by the surgeon.

Moreover, the system, by virtue of the algorithms used and in particular by minimizing the distortion between the real base points and their images in the 2D sections or the maps, makes it possible to establish a two-way coupling between the real world and the computer world through which the transfer errors are minimized, making possible concrete exploitation of the imaging data in order to steer the intervention tool.

To summarize, the system makes possible an ineractive [sic] medical usage not only to create a three-dimensional model of the nonhomogeneous structure but also to permit a marking in real time with respect to the internal structures and to guide the surgeon in the intervention phase.

More generally, the invention makes it possible to end up with a coherent system in respect of:

the two-dimensional imaging data (scanner sections, maps, etc.)

the three-dimensional data base;

the data supplied by the marker means 3 in the reference frame $R_2$;

the coordinate data for the sighting systems and intervention tools;

the real world of the patient on the operating table.

Accordingly, the options offered by the system are, in a non-limiting manner, the following:

the tools and of [sic] their position can be represented on the screen;

the position of a point on the screen can be materialized on the patient for example with the aid of the laser emission device EL;

the orientation and the path of a tool such as a needle can be represented on the screen and materialized on the patient optically (laser emission) or mechanically (positioning of the guide-arm in which the tool is guided in translation):

an image of the patient, yielded for example by a system for taking pictures if appropriate in relief, can be superimposed on the three-dimensional representation modeled on the screen; thus, any change in the soft external parts of the patient can be visualized as compared with the capture by the scanner;

it being possible for the surgeon's field of view given by a sighting member (such as a surgical microscope) to be referenced with respect to $R_2$, the direction of visualization of the model on the screen can be made identical to the real sight by the sighting member;

finally, the three-dimensional images, normally displayed on the screen in the preceding description, may as a variant be introduced into the surgeon's microscope so as to obtain the superposition of the real image and the representation of the model.

We claim:

1. An interactive system for local intervention inside a region of a non-homogeneous structure to which is connected a reference structure containing a plurality of base points, the interactive system comprising:

means for dynamically displaying a three-dimensional image of a representation of the non-homogeneous structure and of the reference structure connected to the non-homogeneous structure, wherein the three-dimensional image also includes a plurality of images of the plurality of base points;

means for determining a set of coordinates of the plurality of images of the plurality of base points in a first reference frame;

means for fixing a position of the non-homogeneous structure and of the reference structure with respect to a second reference frame;

means for determining a set of coordinates of the plurality of base points in the second reference frame;

means of intervention comprising an active member whose position is determined with respect to the second reference frame;

means for generating a plurality of reference frame translation tools for translating a plurality of reference frames from the first reference frame to the second reference frame and vice versa, based on the set of coordinates of the plurality of images of the plurality of base points in the first reference frame and of the set of coordinates of the plurality of base points in the second reference frame, in such a way as to reduce to a minimum at least one of a set of deviations between the set of coordinates of the plurality of images of the plurality of base points in the first reference frame and the set of coordinates of the base points, expressed in the first reference frame using the plurality of reference frame translation tools;

means for defining, with respect to the first reference frame, a simulated origin of intervention and a simulated direction of intervention; and, means for transferring the plurality of reference frames using the plurality of reference frame translation tools to establish a bidirectional coupling between the simulated origin of intervention and the simulated direction of intervention and the position of the active member.

2. The interactive system according to claim 1, wherein the plurality of reference frame translation tools comprise:

means for creating a matrix (M) for transferring between the first reference frame and a first intermediate reference frame based on a set of coordinates of a set of three images of a set of three base points of the reference structure;

means for creating a matrix (N) for transferring between the second reference frame and a second intermediate reference frame based on the set of coordinates of the set of three images of the set of three base points of the reference structure; and, means for validating matrix (M) and matrix (N) based on the set of three base points and the set of three images, such that at least one deviation between an expression for at least one additional base point in the second intermediate reference frame and an expression for at least one image point of the additional base point in the first intermediate reference frame is reduced to a minimum.

3. The interactive system according to plurality of claim 2, wherein the means for transferring the reference frames using the plurality of reference frame translation tools further comprises:

a first transfer sub-module for transferring a set of representation/non-homogeneous structure coordinates, and a second transfer sub-module for transferring a set of non-homogeneous structure/representation coordinates.

4. The interactive system according to claim 3, wherein the first transfer sub-module comprises:

means for acquiring a set of coordinates (XM, YM, ZM), expressed in the first reference frame, of a point of the representation of the non-homogeneous structure to be transferred, by selection on the representation;

means for calculating a set of corresponding coordinates (XP, YP, ZP), expressed in the second reference frame, on the non-homogeneous structure through a transformation:

$\{YP, YP, ZP\} = M*N^{-1} * \{XM, YM, ZM\}$ where $M * N^{-1}$ represents a product of the matrix (M) and an inverse of the matrix (N), and means for processing, with the aid of the corresponding coordinates (YP, YP, ZP), to display a corresponding point on a surface of the non-homogeneous structure and to secure the intervention.

5. The interactive system according to claim 3, wherein the second transfer sub-module comprises:

means for acquiring a set of coordinates (XP, YP, ZP), expressed in the second reference frame, of a point of the non-homogeneous structure to be transferred;

means for calculating a set of corresponding coordinates (XM YM, ZM), expressed in the first reference frame, of the representation through a transformation:

$\{YM, YM, ZM\} = N*M^{-1} * \{XP, ZP, ZP\}$ where $N*M^{-1}$ represents the product of the matrix (N) and an inverse of the matrix (M); and, means for displaying the representation using the set of corresponding coordinates (YM, YM, ZM).

6. The interactive system according to claim 1, wherein the means for generating the plurality of reference frame translation tools also generate, in association with the reference frame translation tools, tools for taking into account a residual uncertainty which is based on the set of deviations between the set of coordinates of the plurality of images of the plurality of base points in the first reference frame and the set of coordinates of the base points, the tools for taking into account the residual uncertainty usable for displaying a set of contours in the representation whilst taking into account the residual uncertainties.

7. The interactive system according to claim 1, wherein the means of dynamic displaying the three-dimensional image comprises:

a file containing digitized data from a set of two-dimensional images constituted by successive non-invasive tomographic sections of the non-homogeneous structure;

means for calculating and reconstructing the three-dimensional image from the set of two-dimensional images; and a high-resolution display screen.

8. The interactive system according to claim 7, wherein the means for calculating and reconstructing the three-dimensional image from the set of two-dimensional images comprises a program consisting of computer-aided design type software.

9. The interactive system according to claim 1, wherein the means for determining the set of coordinates of the plurality of base points in the second reference frame comprises a three-dimensional probe equipped with a tactile tip for delivering a set of coordinates of the tactile tip in the said second reference frame.

10. The interactive system according to claim 1, wherein the means for determining the set of coordinates of the plurality of base points is the second reference frame comprises at least one of a set of optical sensors and a set of electromagnetic sensors.

11. The interactive system according to claim 1, wherein a portion of the set of the plurality of base points of the reference structure comprises a plurality of marks positioned on a lateral surface of the non-homogeneous structure.

12. The interactive system according to claim 11, wherein the plurality of marks are four in number and are distributed over the lateral surface so as to define a substantially symmetrical tetrahedron.

13. The interactive system according to claim 1, wherein the means of intervention comprises:

a guide arm to secure intervention in the region of the non-homogeneous structure, the guide arm having a position marked with respect to the second reference frame; and, an active intervention member whose position is marked with respect to the second reference frame.

14. The interactive system according to claim 13, wherein the active intervention member is removable and selected from the group consisting of:

tools for trephining;

needles and implants;

laser and radioisotope emission heads; and, sighting and viewing systems.

15. The interactive system according to claim 1, wherein the means for transferring the plurality of reference frames establishes a coupling between a direction of visualization of the representation of the non-homogeneous structure on the display means and a direction of observation of the non-homogeneous structure and of the reference structure by the active intervention member.

16. The interactive system according to claim 15, further comprising:

a first module for visualizing a representation in a direction given by two points;

a second module for visualizing a representation in a direction given by an angle of elevation and an angle of azimuth.

* * * * *

UNITED STATES PATENT AND TRADEMARK OFFICE
CERTIFICATE OF CORRECTION

PATENT NO.: 5,868,675
DATED: February 9, 1999
INVENTOR(S): Henrion et al.

*It is certified that error appears in the above-identified patent and that said Letters Patent is hereby corrected as shown below:*

In the Title, item [54], delete "NONHUMOGENEOUS STRUCTURE" and insert -- NON-HOMOGENEOUS STRUCTURE --.

At item [22], the PCT filing date, delete "May 10, 1990" and insert -- October 5, 1990 --.

Signed and Sealed this

Eighth Day of May, 2001

*Attest:*

NICHOLAS P. GODICI

*Attesting Officer*          *Acting Director of the United States Patent and Trademark Office*